US008882113B2

(12) United States Patent
Porter et al.

(10) Patent No.: US 8,882,113 B2
(45) Date of Patent: Nov. 11, 2014

(54) BIT HOLDERS

(75) Inventors: Douglas Roy Porter, Salem, OR (US); Jason Dean Braunberger, Clackamas, OR (US)

(73) Assignee: WestPort Medical, Inc., Salem, OR (US)

( * ) Notice: Subject to any disclaimer, the term of this patent is extended or adjusted under 35 U.S.C. 154(b) by 1251 days.

(21) Appl. No.: 12/717,068

(22) Filed: Mar. 3, 2010

(65) Prior Publication Data

US 2010/0225073 A1 Sep. 9, 2010
US 2013/0214495 A9 Aug. 22, 2013

Related U.S. Application Data

(63) Continuation-in-part of application No. 11/595,540, filed on Nov. 9, 2006, now abandoned.

(60) Provisional application No. 61/209,137, filed on Mar. 3, 2009.

(51) Int. Cl.
| B23B 31/107 | (2006.01) |
| B23B 31/22 | (2006.01) |
| B23B 31/06 | (2006.01) |
| B25B 23/00 | (2006.01) |
| A61C 1/14 | (2006.01) |
| A61B 17/16 | (2006.01) |
| A61B 17/00 | (2006.01) |

(52) U.S. Cl.
CPC ......... B23B 31/1071 (2013.01); B25B 23/0035 (2013.01); A61B 17/162 (2013.01); A61C 1/142 (2013.01); B23B 2260/078 (2013.01); A61B 2017/00473 (2013.01); Y10S 279/905 (2013.01)
USPC ................ 279/75; 279/22; 279/30; 279/905; 279/155

(58) Field of Classification Search
USPC ................ 279/22, 30, 75, 902, 904, 905, 155
See application file for complete search history.

(56) References Cited

U.S. PATENT DOCUMENTS

| 880,529 | A | * | 3/1908 | Heynau | ........................... 408/73 |
| 1,177,869 | A | * | 4/1916 | Kelly | ............................. 279/38 |

(Continued)

FOREIGN PATENT DOCUMENTS

| JP | 2004050352 | 2/2004 |
| WO | 2008060434 | 5/2008 |
| WO | 2010102062 | 9/2010 |

OTHER PUBLICATIONS

PCT (Blaine R. Copenheaver, authorized officer); "International Search Report" for application No. PCT/US2007/23521 (publication No. WO 2008/060434); mailing date May 20, 2008; 2 pages.

(Continued)

*Primary Examiner* — Eric A Gates
*Assistant Examiner* — Paul M Janeski
(74) *Attorney, Agent, or Firm* — Kolisch Hartwell, PC

(57) ABSTRACT

A holder for a bit is disclosed. The bit may include a first locking element. The holder may include a housing; a base assembly including a first hole; a second locking element partially disposed within the first hole and configured to move between a locking position in which the second locking element engages the first locking element to prevent removal of the bit, and an unlocking position in which the second locking element is spaced from the first locking element allowing the bit to be removed; and a follower assembly contained within the housing and configured to move relative to the housing and base assembly between a first position in which the follower assembly supports the second locking element in the locking position, and a second position in which the follower assembly allows the second locking element to move from the locking position to the unlocking position.

15 Claims, 3 Drawing Sheets

(56) References Cited

U.S. PATENT DOCUMENTS

| | | | | |
|---|---|---|---|---|
| 1,433,590 | A | * | 10/1922 | Ziegler .......................... 279/35 |
| 1,502,528 | A | * | 7/1924 | Reulbach ..................... 279/103 |
| 1,589,287 | A | * | 6/1926 | Ziegler .......................... 279/54 |
| 2,141,786 | A | * | 12/1938 | Helgerud ..................... 408/140 |
| 2,405,772 | A | | 8/1946 | Adams et al. |
| 2,751,229 | A | | 6/1956 | Schultz |
| 3,251,605 | A | | 5/1966 | Ondeck |
| 3,341,213 | A | * | 9/1967 | Lang ............................ 279/103 |
| 3,398,965 | A | | 8/1968 | Cox |
| 3,521,895 | A | | 7/1970 | Smith |
| 3,524,227 | A | * | 8/1970 | Kelly ......................... 24/115 R |
| 3,652,099 | A | * | 3/1972 | Bilz ............................... 279/75 |
| 3,724,056 | A | * | 4/1973 | Antal ............................ 29/253 |
| 3,767,218 | A | | 10/1973 | Linthicum et al. |
| 3,868,748 | A | * | 3/1975 | Kelly ........................ 24/115 M |
| 4,199,160 | A | | 4/1980 | Bent |
| 4,209,182 | A | | 6/1980 | Sheldon |
| 4,234,277 | A | | 11/1980 | Benson et al. |
| 4,577,875 | A | | 3/1986 | Miyakawa |
| 4,626,152 | A | | 12/1986 | Palm |
| 4,688,975 | A | | 8/1987 | Palm |
| 4,692,073 | A | | 9/1987 | Martindell |
| 4,858,939 | A | | 8/1989 | Riggs |
| 4,946,179 | A | | 8/1990 | De Bastiani et al. |
| 5,013,194 | A | | 5/1991 | Wienhold |
| 5,062,749 | A | | 11/1991 | Sheets |
| 5,188,378 | A | | 2/1993 | Erlenkeuser |
| 5,222,956 | A | * | 6/1993 | Waldron ......................... 606/80 |
| 5,398,946 | A | | 3/1995 | Quiring |
| 5,464,229 | A | | 11/1995 | Salpaka |
| 5,709,391 | A | | 1/1998 | Arakawa et al. |
| 5,884,541 | A | * | 3/1999 | Habermehl et al. ............ 81/438 |
| 5,957,634 | A | | 9/1999 | Carpinetti |
| 6,062,779 | A | | 5/2000 | Sugimura |
| 6,179,302 | B1 | | 1/2001 | Gauthier et al. |
| 6,199,872 | B1 | | 3/2001 | Hasan |
| 6,270,085 | B1 | | 8/2001 | Chen et al. |
| 6,270,087 | B1 | * | 8/2001 | Mickel et al. .................. 279/75 |
| 6,311,989 | B1 | | 11/2001 | Rosanwo |
| 6,325,393 | B1 | | 12/2001 | Chen et al. |
| 6,457,916 | B2 | | 10/2002 | Wienhold |
| 6,561,523 | B1 | | 5/2003 | Wienhold |
| 6,612,586 | B2 | | 9/2003 | Liou |
| 6,637,755 | B2 | | 10/2003 | Chen et al. |
| 6,695,321 | B2 | | 2/2004 | Bedi et al. |
| 6,719,619 | B2 | | 4/2004 | Kuo et al. |
| 6,722,667 | B2 | | 4/2004 | Cantlon |
| 6,874,791 | B2 | | 4/2005 | Chen et al. |
| 6,953,196 | B1 | | 10/2005 | Huang |
| 6,966,562 | B1 | | 11/2005 | Wienhold |
| 7,424,841 | B2 | | 9/2008 | Liu |
| 7,448,302 | B2 | | 11/2008 | Huang |
| 7,581,470 | B1 | | 9/2009 | Huang |
| 2001/0043841 | A1 | | 11/2001 | Wienhold |
| 2004/0026878 | A1 | | 2/2004 | Chen et al. |
| 2004/0094908 | A1 | | 5/2004 | Cantlon |
| 2004/0164503 | A1 | | 8/2004 | Fan-Chiang et al. |
| 2004/0262856 | A1 | | 12/2004 | Cantlon |
| 2005/0116429 | A1 | | 6/2005 | Chang |
| 2007/0204730 | A1 | * | 9/2007 | Rajotte .......................... 81/429 |
| 2008/0111323 | A1 | | 5/2008 | Braunberger |

OTHER PUBLICATIONS

PCT (Blaine R. Copenheaver, authorized officer); "Written Opinion of the International Searching Authority" for application No. PCT/US2007/23521 (publication No. WO 2008/060434); mailing date May 20, 2008; 6 pages.

PCT (Beate Giffo-Schmitt, authorized officer); "International Preliminary Report on Patentability" for application No. PCT/US2007/23521 (publication No. WO 2008/060434); mailing date May 12, 2009; 6 pages.

PCT (Blaine R. Copenheaver, authorized officer); "International Search Report" for application No. PCT/US2010/026124 (publication No. WO 2010/102062); mailing date May 21, 2010; 3 pages.

PCT (Blaine R. Copenheaver, authorized officer); "Written Opinion of the International Searching Authority" for application No. PCT/US2010/026124 (publication No. WO 2010/102062); mailing date May 21, 2010; 7 pages.

PCT (Nora Lindner, authorized officer); "International Preliminary Report on Patentability" for application No. PCT/US2010/026124 (publication No. WO 2010/102062); mailing date Sep. 6, 2011; 8 pages.

USPTO (Eric A. Gates, authorized officer); "Office Action" for U.S. Appl. No. 11/595,540; mailing date Jul. 29, 2010; 24 pages.

* cited by examiner

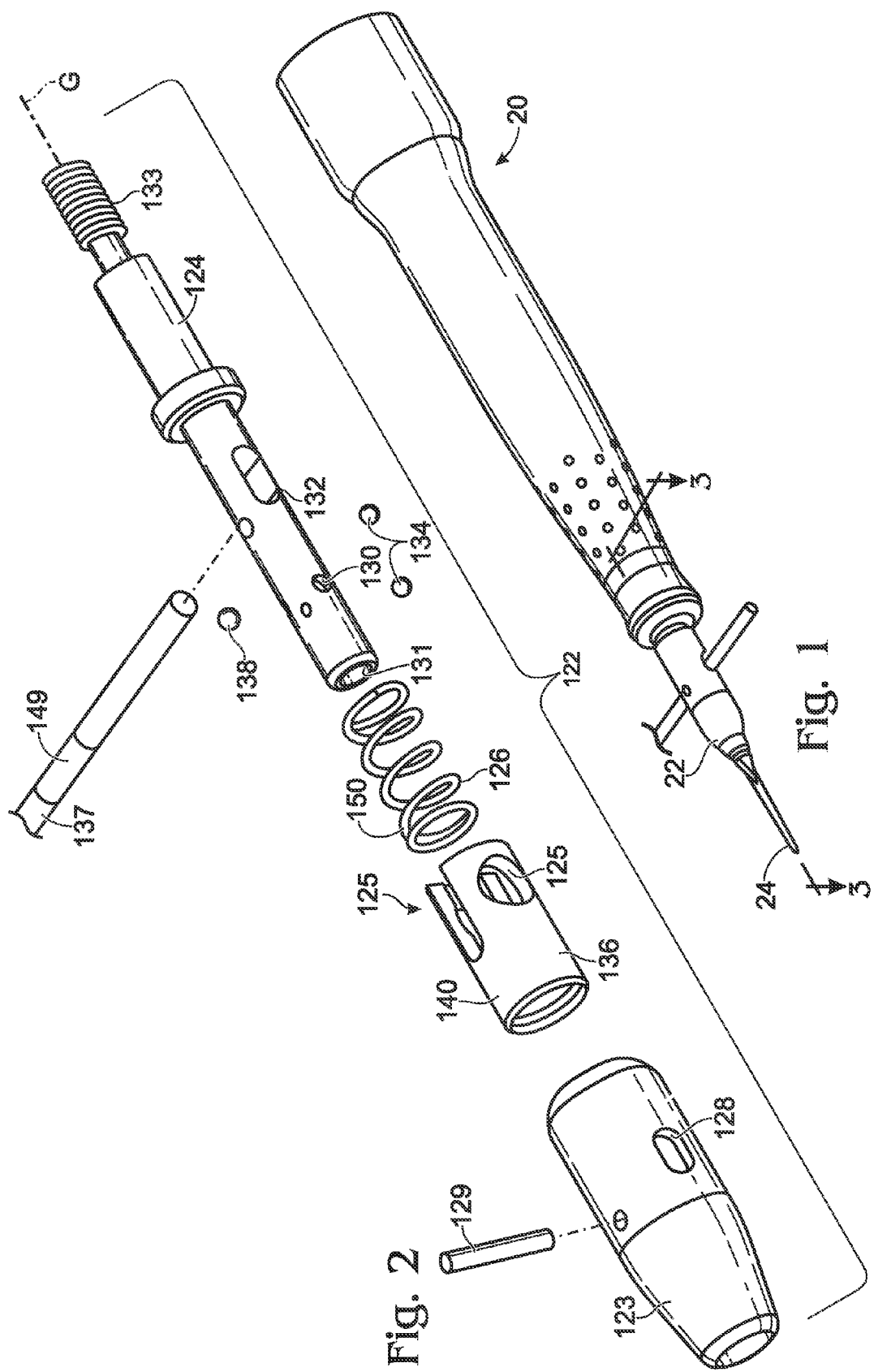

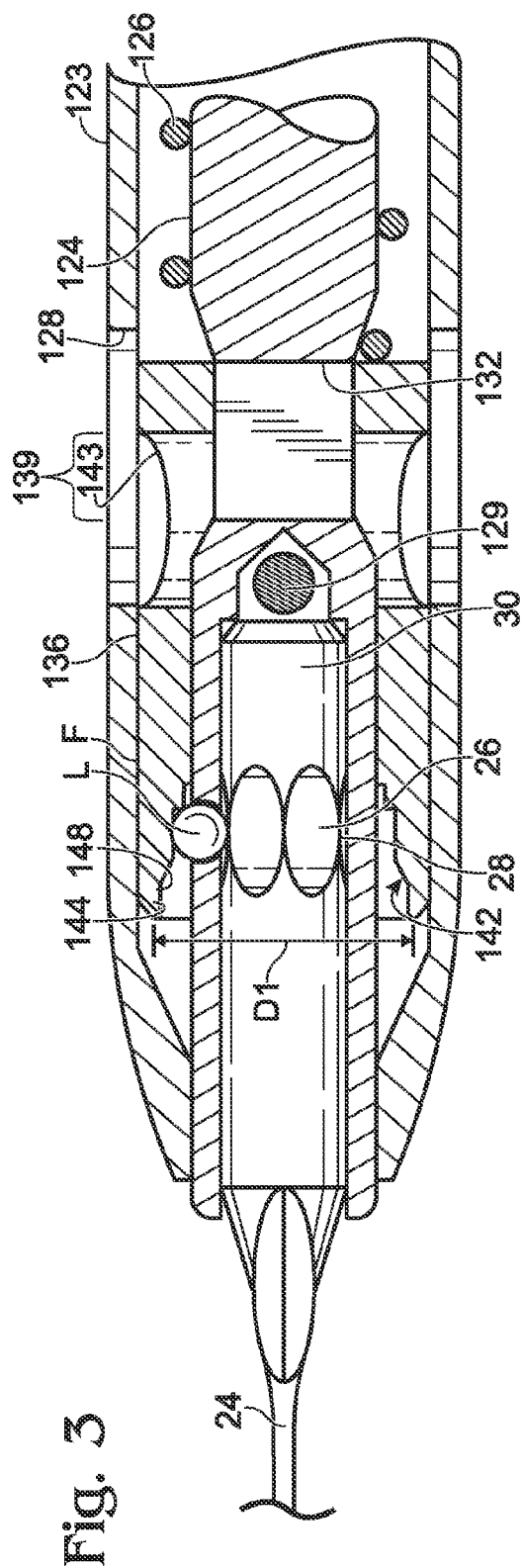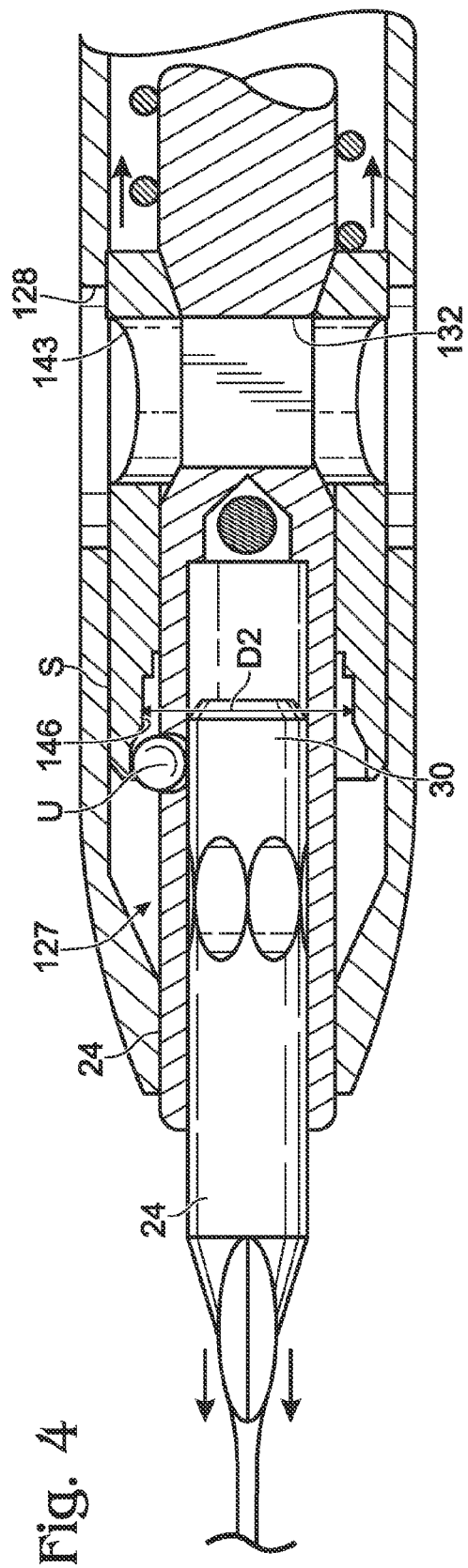

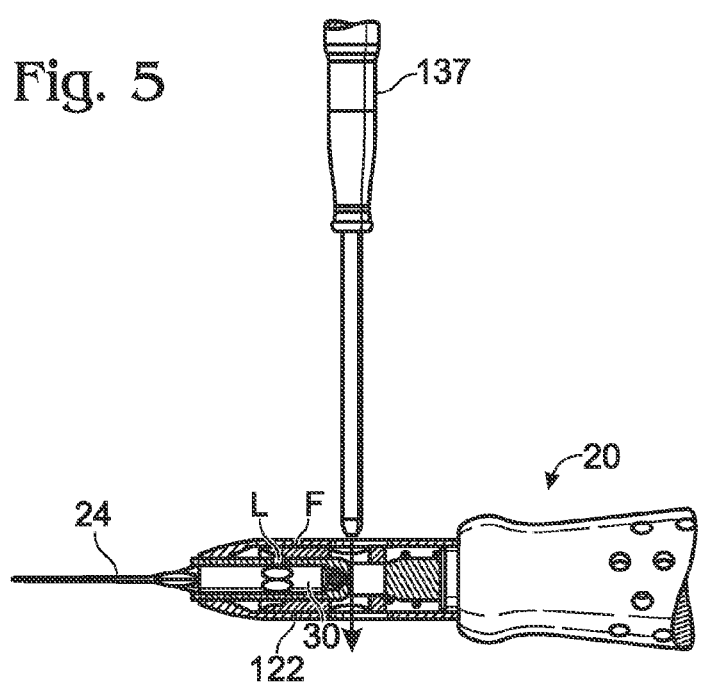
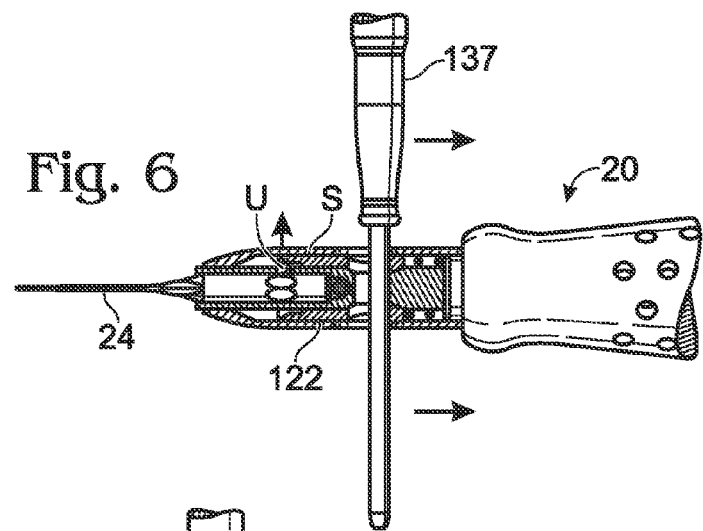
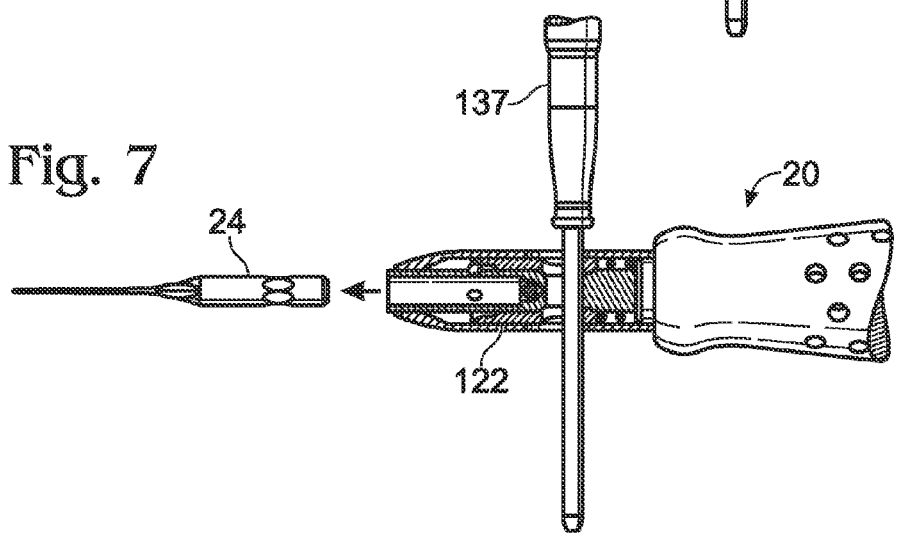

BIT HOLDERS

CROSS-REFERENCE TO RELATED APPLICATIONS

This application is a continuation-in-part of U.S. patent application Ser. No. 11/595,540, filed Nov. 9, 2006 now abandoned and entitled "Bit Holders." Additionally, this application claims priority under 35 U.S.C. §119(e) to U.S. Provisional Patent Application Ser. No. 61/209,137 entitled "Bit Holders," filed Mar. 3, 2009. The complete disclosure of the above provisional application is herein incorporated by reference for all purposes.

BACKGROUND OF THE DISCLOSURE

Various powered and/or manual instruments may use one or more removable tool bits, which may have different shapes and/or designs to accomplish different tasks. The instruments typically will include a bit holder to removably hold and/or secure one or more of the bits. Some bit holders may require manipulation by the user to secure and/or unsecure the desired bit to the bit holder. For example, a conventional three-jaw chuck requires the user to loosen the jaws to insert or remove the bit and to tighten the jaws to secure the bit. Other bit holders may automatically secure and/or lock the bit when the user inserts the bit into the bit holder. Alternatively, bit holders may require an external device, such as a key or tool, to secure and/or unsecure the bit to the bit holder.

Examples of bit holders may be found in U.S. Pat. Nos. 3,521,895; 3,767,218; 4,199,160; 4,209,182; 4,234,277; 4,626,152; 4,688,975; 4,692,073; 4,858,939; 4,946,179; 5,013,194; 5,062,749; 5,188,378; 5,398,946; 5,464,229; 5,709,391; 5,957,634; 6,062,779; 6,199,872; 6,270,085; 6,325,393; 6,311,989; 6,561,523; 6,612,586; 6,695,321; and 6,719,619; U.S. Patent Application Publication No. 2005/0116429; and Japanese Patent Application Publication No. JP2004050352. The complete disclosures of the above patents and patent application publications are herein incorporated by reference for all purposes.

SUMMARY OF THE DISCLOSURE

Some embodiments provide a holder for a bit. The bit may include a first locking element. The holder may include a housing; a base assembly attached to the housing, the base assembly including a first hole and a second hole sized to receive a portion of the bit; a second locking element partially disposed within the first hole and configured to move between a locking position in which the second locking element engages the first locking element to prevent removal of the bit from the second hole of the base assembly, and an unlocking position in which the second locking element is spaced from the first locking element allowing the bit to be removed from the second hole of the base assembly; and a follower assembly contained within the housing and configured to move relative to the housing and base assembly between a first position in which the follower assembly supports the second locking element in the locking position, and a second position in which the follower assembly allows the second locking element to move from the locking position to the unlocking position.

Some embodiments provide a holder for a bit. The bit may include at least one groove. The holder may include a housing; a base assembly attached to the housing, the base assembly including at least one radial hole and a longitudinal hole sized to receive a portion of the bit; at least one ball partially disposed within the at least one radial hole and configured to move between a locking position in which the at least one ball engages the at least one groove to prevent removal of the bit from the longitudinal hole of the base assembly, and an unlocking position in which the at least one ball is spaced from the at least one groove allowing the bit to be removed from the longitudinal hole of the base assembly; a follower assembly contained within the housing and disposed between the base assembly and the housing, the follower assembly being configured to slide relative to the housing and the base assembly between a first position in which the follower assembly supports the at least one ball in the locking position, and a second position in which the follower assembly allows the at least one ball to move from the locking position to the unlocking position; and a bias element disposed between the base assembly and the housing and configured to urge the follower assembly toward the first position.

Some embodiments provide a holder for a bit. The bit may include at least one groove. The holder may include a housing; a base assembly attached to the housing, the base assembly including a plurality of radial holes and a longitudinal hole sized to receive a portion of the bit; at least three balls each partially disposed within one of the plurality of radial holes, the at least three balls configured to move between a locking position in which the at least three balls engage the at least one groove to prevent removal of the bit from the longitudinal hole of the base assembly, and an unlocking position in which the at least three balls are spaced from the at least one groove allowing the bit to be removed from the longitudinal hole of the base assembly; a sleeve contained within the housing and disposed between the base assembly and the housing, the sleeve being configured to move relative to the housing and the base assembly between a first position in which the sleeve supports the at least three balls in the locking position, and a second position in which the sleeve allows the at least three balls to move from the locking position to the unlocking position; and a coil spring disposed between the base assembly and the housing and configured to urge the sleeve toward the first position, wherein the housing includes an aperture configured to provide access to the sleeve to allow a user to move the sleeve between the first and second positions from external the housing.

BRIEF DESCRIPTION OF THE DRAWINGS

FIG. 1 is a powered surgical instrument having a bit holder.

FIG. 2 is an exploded view of an illustrative example of a bit holder of the powered surgical instrument of FIG. 1.

FIG. 3 is a partial sectional view of the bit holder of FIG. 2 taken along lines 3-3 in FIG. 1, showing the bit holder with a bit locked to the bit holder.

FIG. 4 is the partial sectional view of FIG. 3, showing the bit unlocked from the bit holder.

FIGS. 5-7 are the sectional views of FIG. 3, showing use of a tool to unlock and remove a bit from the bit holder.

DETAILED DESCRIPTION OF THE DISCLOSURE

FIG. 1 depicts a powered surgical instrument 20 having a bit holder 22 that removably secures a bit 24. The powered surgical instrument may have any suitable structure and/or may have any suitable function(s). For example, powered surgical instrument 20 may include at least some of the components described in U.S. Patent Application Publication No. 2006/0014119. The complete disclosure of that publication is herein incorporated by reference for all purposes. Although powered surgical instrument 20 is shown to include bit holder 22, any suitable powered and/or manual instrument may include the bit holder.

Bit 24 may include one or more first locking elements 26 (as shown in FIG. 3), which may include, any suitable structure configured to interact with one or more locking mechanisms of the bit holder. For example, first locking elements 26 may include one or more indentations, depressions, or grooves 28. Grooves 28 may include any suitable shape(s). For example, the grooves may include approximately capsule-like depressions, such as the grooves shown in U.S. Design Pat. No. D568,474. The complete disclosure of that patent is herein incorporated by reference for all purposes.

Although first locking elements 26 are shown to include one or more indentations or grooves 28, the first locking elements may include any suitable structure configured to interact with one or more locking mechanisms of the bit holder. For example, first locking elements 26 may alternatively, or additionally, include one or more ridges, one or more ribs, etc. Additionally, although grooves 28 are shown to include approximately capsule-like depressions, the grooves may include any suitable shape(s). Moreover, although grooves 28 are shown to include discrete shapes, the grooves may alternatively, or additionally, include one or more continuous shape(s), such as one or more circumferential grooves. Furthermore, although grooves 26 are shown to be adjacent to each other, one or more of the grooves may be spaced from each other at any suitable distance(s).

An illustrative example of bit holder 22 is shown in FIGS. 2-5 and is generally indicated at 122. Bit holder 122 may include any suitable structure configured to removably secure one or more bits to the powered surgical instrument or any suitable instrument. For example, bit holder 122 may include a housing 123, at least one base assembly 124, at least one locking mechanism 125, and at least one bias assembly 126, as shown in FIGS. 2-3.

The housing may include any suitable structure configured to contain, enclose, and/or support the other components of the bit holder. For example, housing 123 may include an internal cavity 127, at least one aperture 128, and a bit stop 129, as shown in FIG. 3. The internal cavity may receive, contain, and/or support one or more other components of the bit holder.

Aperture 128 may be in any suitable portion of the housing and may be configured to allow access to one or more other components (such as the follower assembly) of the bit holder from external the housing. For example, at least one component may be completely contained and/or enclosed by the housing and/or one or more other component(s) of the bit holder and the only way to access that component from external the housing is through the aperture. That limited access may ensure that the component enclosed is not inadvertently moved and/or activated during operation. For example, when the component enclosed is the follower assembly, the limited access to that assembly may prevent the bit from being inadvertently ejected during operation.

The aperture may extend through the housing or any suitable portion(s) of the housing. In other words, the aperture may extend from a first surface of the housing to a second surface of the housing. The first and second surfaces may be in any suitable portion(s) of the housing. For example, the first and second surfaces may be outer surfaces of the housing, such as on opposite outer surfaces along a radial axis of the housing. When the aperture extends through the housing (may sometimes be referred to as a "through aperture" or "through hole"), an external implement may be inserted into the aperture and through the housing. Alternatively, when the aperture does not extend through the housing, an external implement may be inserted into the aperture but not through the housing.

Bit stop 129 may include any suitable structure configured to ensure proper positioning of the bit into a second hole of the base assembly (further discussed below) such that at least a portion of locking mechanism 125 is adjacent to the bit when the bit is inserted into the second hole. The bit stop also may secure and/or attach the base assembly to the housing. Bit stop 129 may sometimes be referred to as a "spring roll pin."

Base assembly 124 may be positioned within the internal cavity and/or attached to the housing. The base assembly may include any suitable structure configured to support bit 24. For example, base assembly 124 may include one or more first holes 130, at least one second hole 131, at least one third hole 132, and at least one instrument connecting portion 133, as shown in FIG. 1. The first holes may be configured to support one or more components of the locking mechanism, such as one or more locking elements as further discussed below. First holes 130 may be sized to allow movement of one or more of the locking elements within any suitable range(s) and/or direction(s). For example, the first holes may be sized to allow one or more of the locking elements to move radially without falling into the second hole, as shown in FIG. 3. In some embodiments, the first holes may be bored partially through the base assembly to locate the locking elements.

First holes 130 may include any suitable number of holes, such as three holes. Additionally, when first holes 130 include two or more holes, those holes may be spaced from each other at any suitable distance(s). Second hole 131 may be sized to receive at least a portion of the bit, such as an end portion 30 of bit 24, as shown in FIG. 3. Third hole 132 may be adjacent to aperture 128 of the housing and may be sized to receive a tool of the locking mechanism (as further discussed below).

First holes 130, second hole 131, and/or third hole 132 may have any suitable orientation(s). For example, the first holes and/or the third hole may be oriented in a radial direction of the bit holder (also may be referred to as radial holes). Additionally, or alternatively, second hole 131 may be oriented in a longitudinal direction (also may be referred to as a longitudinal hole), such as along a longitudinal axis L defined by the base assembly. Instrument connecting portion 133 may include any suitable structure configured to connect base assembly 124 to the powered surgical instrument, such as one or more threaded sections.

Although base assembly 124 is shown to include first holes 130, second hole 131, and third hole 132, the base assembly may include any suitable number of holes that may be more or less than the holes shown in FIG. 3. For example, base assembly may include a single first hole 130, a single second hole 131, and a single third hole 132. Additionally, although first holes 130 and third hole 132 are shown to be oriented in the radial direction, the first and/or third holes may alternatively, or additionally, be oriented in any suitable direction(s), such as a longitudinal direction. Moreover, although second hole 131 is shown to be oriented in the longitudinal direction, the second hole may be oriented in any suitable direction(s), such as a radial direction.

Furthermore, although base assembly 124 is shown to include particular structure, the base assembly may alternatively, or additionally, include any suitable structure. For example, base assembly 124 may include at least one collet (not shown), which may include another hole (not shown) sized to receive at least a portion of the bit, such as an end portion 30 of bit 24. In some embodiments, the use of a collet may enable the bit holder to accept bits with different diameters.

Locking mechanism 125 may include any suitable structure configured to secure the bit to base assembly 124. For example, the locking mechanism may include one or more second locking elements 134, at least one follower assembly 136, and at least one tool 137, as shown in FIG. 2. The second locking elements may be at least partially disposed within one or more of the first holes of the base assembly.

Additionally, second locking elements 134 may move within the first holes among a plurality of positions, as shown in FIGS. 3-4. For example, second locking elements 134 may move between a locking position L (shown in FIG. 3) in which one or more of the second locking elements may engage at least a portion of one or more of the first locking elements to prevent removal of the bit from the second hole of the base assembly, and an unlocking position U (shown in FIG. 4) in which one or more of the second locking elements may be spaced from one or more of the first locking elements allowing the bit to be removed from the second hole of the base assembly.

Second locking elements 134 may include any suitable structure configured to engage at least a portion of first locking element 26. For example, second locking elements 134 may include at least one interference member, such as at least one ball 138, as shown in FIG. 2. The second locking elements may include any suitable number of balls. For example, second locking elements 134 may include three balls. Engagement of the first and second locking elements may allow locking of the bit in the axial and radial directions, which may ensure that the bit does not inadvertently rotate while being used.

Although second locking elements 134 are shown to be configured to move between locking position L and unlocking position U, one or more of the second locking elements may alternatively, or additionally, be configured to move among other suitable position(s). Additionally, although second locking elements 134 are shown to include balls 138, the second locking elements may include any suitable structure configured to engage at least a portion of one or more of the first locking elements. For example, second locking elements 134 may alternatively, or additionally, include one or more pins, one or more levers, one or more arms, one or more disks, etc.

Moreover, although second locking elements 134 are shown to include three balls 138, the second locking elements may include any suitable number of balls, which may be more or less than the balls shown. Furthermore, although each ball 138 is shown to be at least partially disposed within a different first hole 130, two or more of the balls may be partially disposed within one or more of the first holes 130.

Follower assembly 136 may be movably and/or operatively connected to the base assembly. For example, the follower assembly may be contained and/or enclosed within the housing, and/or may be disposed between the base assembly and the housing. In some embodiments, the follower assembly may be completely contained and/or enclosed within the housing. In those embodiments, the follower assembly may be accessed external the housing via only one or more apertures (further discussed below). In other embodiments, one or more portions of the follower assembly may be external the housing.

Additionally, the follower assembly may be configured to move relative to the housing and/or base assembly among a plurality of positions. For example, follower assembly 136 may be configured to move between a first position F (shown in FIG. 3) in which the follower assembly may support one or more of the second locking elements in the locking position, and a second position S (shown in FIG. 4) in which the follower assembly may allow one or more of the second locking elements to move from the locking position toward the unlocking position.

The follower assembly may be movably connected to the base assembly in any suitable way(s). For example, follower assembly 136 may be slidingly connected to the base assembly such that the follower assembly slides among one or more of the plurality of positions. Although follower assembly 136 is shown to be configured to move between the first position and the second position, the follower assembly may alternatively, or additionally, be configured to move among one or more other suitable positions. Additionally, although follower assembly 136 is shown to be slidingly connected to base assembly 124, the follower assembly may alternatively, or additionally, be pivotally connected, rotatingly connected, and/or connected in other suitable way(s).

Follower assembly 136 may include any suitable structure configured to move one or more of the second locking elements and/or allow one or more of the second locking elements to move among the plurality of positions, such as between locking position L and unlocking position U. For example, follower assembly 136 may include at least one sleeve 140.

Sleeve 140 may include at least one internal surface or wall 142 and at least one opening 143, as shown in FIGS. 3-4. The internal wall may include a first portion 144, a second portion 146, and at least one sloped transition portion 148. The first and/or second portions may have any suitable diameter(s). For example, first portion 144 may have a first diameter D1 and second portion 146 may have a second diameter D2. First diameter D1 may be larger than second diameter D2, as shown in FIG. 3. Alternatively, the first diameter may be equal to or smaller than the second diameter.

Sloped transition portion 148 may be disposed between first portion 144 and second portion 146. Additionally, or alternatively, the sloped transition portion may contact one or more of the second locking elements. Alternatively, or additionally, sloped transition portion 148 may move one or more of the second locking elements from the unlocking position to the locking position when the sleeve is moved from the second position to the first position. The sloped transition portion also may be referred to as a slanted internal surface.

Additionally, or alternatively, the sloped transition portion may be spaced from one or more of the second locking elements when the sleeve is in the second position. In some embodiments, movement of the sleeve from the first position toward the second position may allow one or more of the second locking elements to move from the locking position toward the unlocking position because of, for example, urging of the bit away from the second hole by the bias assembly.

Opening 143 may be sized to receive an external implement, such as tool 137, and allow movement of the sleeve between the first and second positions via insertion of the tool into the opening and movement of the tool. The opening may extend through the sleeve or any portion(s) of the sleeve. In other words, the opening may extend from a first surface of the sleeve to a second surface of the sleeve. The first and second surfaces may be in any suitable portion(s) of the sleeve. For example, the first and second surface may be outer surfaces of the sleeve, such as on opposite outer surfaces along a radial axis of the sleeve (perpendicular of the longitudinal axis through the sleeve).

The opening may be adjacent to aperture 128 and third hole 132 in the first and/or second positions of the sleeve. For example, the opening may form an overlap 139 with the aperture and/or the third hole when the aperture is viewed perpendicular to the longitudinal axis. The overlap may be configured to receive an external implement, such as the tool, when the sleeve is in the first and/or second positions. In some embodiments, overlap 139 may be larger (such as larger in diameter or width) when the sleeve is in the second position compared to when the sleeve is in the first position.

In some embodiments, opening 143 may be adjacent to aperture 128 and third hole 132 when sleeve 140 is in the second position. In contrast, opening 143 may be offset from aperture 128 and third hole 132 relative to the second position when the sleeve is in the first position.

Aperture 128, third hole 132, and/or opening 143 may be oriented in any suitable direction(s), such as the radial direction. In some embodiments, orienting the aperture, third hole, and/or opening offset, such as perpendicular, from the direction in which the bit holder moves during operation of the powered surgical instrument may prevent inadvertent movement of the sleeve and release of the bit. For example, if the bit holder moves in the longitudinal direction of the bit holder during operation of the powered surgical instrument, then aperture 128, third hole 132, and/or opening 143 may be oriented perpendicular to that direction.

Aperture 128, third hole 132, and/or opening 143 may have any suitable relative widths (measured parallel to the longitudinal axis). For example, although third hole 132 is shown to include about the same width as the opening (which is smaller the width of the aperture), the third hole may alternatively have approximately the same width as the aperture.

Although sleeve 140 is shown to include internal wall 142 with first portion 144, second portion 146, and sloped transition portion 148, the sleeve may include any suitable structure configured to move and/or allow one or more of the second locking elements to move between the locking position and the unlocking position. For example, sleeve 140 may include one or more balls, one or more arms, and/or one or more levers. Additionally, although follower assembly 136 is shown to include sleeve 140, the follower assembly may include any suitable structure configured to move and/or allow one or more of the second locking elements to move between the locking position and the unlocking position.

Tool 137 may include any suitable structure configured to be received within opening 143 and allow a user to move the sleeve between the first and/or second positions by movement of the tool. For example, tool 137 may include a key 149, as shown in FIG. 2. Although key 149 is shown to be cylindrical in shape, the key may alternatively, or additionally, include any suitable shape(s). Although tool 137 is shown to access the sleeve, the overlap may alternatively, or additionally, be configured to or sized to allow a user's finger to reach into the sleeve to move the sleeve between the first and second positions.

Bias assembly 126 may be operatively connected to the base assembly and may include any suitable structure configured to urge follower assembly 136 toward the first position. For example, bias assembly 126 may include at least one bias element 150, such as a coil spring, as shown in FIG. 2. At least a substantial portion of the bias element may be disposed between the follower assembly and the instrument connecting portion of the base assembly and/or between the base assembly and the housing. Although bias element 150 is shown to be disposed between the follower assembly and the instrument connecting portion of the base assembly, the bias element may be in any suitable location(s) in the bit holder.

Although bias element 150 is shown to include a coil spring, the bias element may include any suitable structure, such as leaf springs, spiral springs, cantilever springs, Belleville springs, spring washers, torsion springs, gas springs, rubber bands, etc. Additionally, although bias assembly 126 is shown to include a single bias element 150, the bias assembly may include two or more bias elements.

Although housing 123, base assembly 124, locking mechanism 125, and bias assembly 126 are shown to be discrete assemblies of bit holder 122, one or more of those assemblies may have one or more common components. For example, sleeve 140 may be incorporated and/or formed with at least a portion of housing 123 such that the sleeve and at least a portion of the housing move relative to the base assembly. Incorporating one or more components with other components may be accomplished through any suitable process(es), such as injection molding and/or machining.

Additionally, although bit holder 122 is shown to include housing 123, base assembly 124, locking mechanism 125, and bias assembly 126, the bit holder may alternatively, or additionally, include any suitable structure configured to removably secure one or more bits to the powered surgical instrument. Removal of the bit from the bit holder is further illustrated in FIGS. 5-7.

The disclosure set forth above encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and non-obvious combinations and subcombinations of the various elements, features, functions and/or properties disclosed herein. Similarly, where any claim recites "a" or "a first" element or the equivalent thereof, such claim should be understood to include incorporation of one or more such elements, neither requiring nor excluding two or more such elements.

Inventions embodied in various combinations and subcombinations of features, functions, elements, and/or properties may be claimed through presentation of new claims in a related application. Such new claims, whether they are directed to a different invention or directed to the same invention, whether different, broader, narrower or equal in scope to the original claims, are also regarded as included within the subject matter of the inventions of the present disclosure.

What is claimed is:

1. A holder for a bit, the bit including a first locking element, comprising:
    a housing;
    a base assembly attached to the housing, the base assembly including a first hole and a second hole sized to receive a portion of the bit;
    a second locking element partially disposed within the first hole and configured to move between a locking position in which the second locking element engages the first locking element to prevent removal of the bit from the second hole of the base assembly, and an unlocking position in which the second locking element is spaced from the first locking element allowing the bit to be removed from the second hole of the base assembly; and
    a follower assembly contained within the housing and configured to move relative to the housing and base assembly between a first position in which the follower assembly supports the second locking element in the locking position, and a second position in which the follower assembly allows the second locking element to move from the locking position to the unlocking position,
    wherein the holder is free from structure that is movably attached to at least one of the housing and the base assembly, and that allows the user to move the follower assembly from the first position toward the second position by moving the structure relative to the at least one of the housing and the base assembly, wherein the housing includes a first aperture and a second aperture, the second aperture being opposed to the first aperture, the first and second apertures being configured to provide access to the follower assembly from external the housing, the follower assembly including a first opening and a second opening, the second opening being opposed to the first opening, wherein, when the follower assembly is in the first position, the first opening overlaps with the first aperture and the second opening overlaps with the second aperture such that a passage is formed through the first and second apertures and the first and second openings, and wherein the formed passage is configured to receive an external implement, the external implement allowing a user to move the follower assembly from the first position toward the second position from external the housing by moving the external implement relative to the housing when the external implement is received in the formed passage.

2. The holder of claim 1, where the base assembly defines a longitudinal axis, wherein the first and second openings overlap with the first and second apertures when the first and second apertures are viewed perpendicular to the longitudinal axis.

3. The holder of claim 1, where the base assembly defines a longitudinal axis, wherein the first and second openings extend perpendicular of the longitudinal axis through the follower assembly.

4. The holder of claim 1, further comprising a bias assembly operatively connected to the follower assembly and configured to urge the follower assembly toward the first position.

5. The holder of claim 4, wherein the bias assembly is disposed between the base assembly and the housing.

6. The holder of claim 4, wherein the bias assembly includes a coil spring.

7. The holder of claim 1, wherein the second locking element includes a ball configured to engage the first locking element in the locking position.

8. The holder of claim 1, wherein the first hole is a radial hole.

9. The holder of claim 8, wherein the second hole is a longitudinal hole.

10. The holder of claim 1, wherein the follower assembly includes a sleeve slidingly connected to the base assembly, the sleeve including an internal wall, the internal wall including a first portion having a first diameter, a second portion spaced from the first portion and having a second diameter that is smaller than the first diameter of the first portion, and a sloped transition portion disposed between the first and second portions, wherein the sloped transition portion contacts the second locking element and moves the second locking element from the unlocking position to the locking position when the sleeve is moved from the second position to the first position.

11. The holder of claim 10, wherein the sloped transition portion is spaced from the second locking element when the sleeve is in the second position allowing the second locking element to move from the locking position to the unlocking position.

12. A holder for a bit, the bit including at least one groove, comprising:
a housing including first and second opposed apertures;
a base assembly attached to the housing, the base assembly including at least one radial hole and a longitudinal hole sized to receive a portion of the bit, the base assembly defining a longitudinal axis;
at least one ball partially disposed within the at least one radial hole and configured to move between a locking position in which the at least one ball engages the at least one groove to prevent removal of the bit from the longitudinal hole of the base assembly, and an unlocking position in which the at least one ball is spaced from the at least one groove allowing the bit to be removed from the longitudinal hole of the base assembly;
a follower assembly contained within the housing and disposed between the base assembly and the housing, the follower assembly being configured to slide relative to the housing and the base assembly between a first position in which the follower assembly supports the at least one ball in the locking position, and a second position in which the follower assembly allows the at least one ball to move from the locking position to the unlocking position; and
a bias element disposed between the base assembly and the housing and configured to urge the follower assembly toward the first position,
wherein the holder is free from structure that is movably attached to at least one of the housing and the base assembly, and that allows the user to move the follower assembly from the first position toward the second position by moving the structure relative to the at least one of the housing and the base assembly,
wherein the follower assembly includes first and second opposed openings that overlap with the first and second apertures when the apertures are viewed perpendicular to the longitudinal axis such that a passage is formed through the first and second apertures and the first and second openings, the first and second openings extending perpendicular of the longitudinal axis through the follower assembly, and
wherein the formed passage is configured to receive an external implement, the external implement allowing a user to move the follower assembly from the first position toward the second position from external the housing by moving the external implement relative to the housing when the external implement is received in the formed passage.

13. A holder for a bit, the bit including at least one groove, comprising:
a housing including first and second opposed apertures;
a base assembly attached to the housing, the base assembly including a plurality of radial holes and a longitudinal hole sized to receive a portion of the bit, the base assembly defining a longitudinal axis;
at least three balls each partially disposed within one of the plurality of radial holes, the at least three balls configured to move between a locking position in which the at least three balls engage the at least one groove to prevent removal of the bit from the longitudinal hole of the base assembly, and an unlocking position in which the at least three balls are spaced from the at least one groove allowing the bit to be removed from the longitudinal hole of the base assembly;
a sleeve contained within the housing and disposed between the base assembly and the housing, the sleeve being configured to move relative to the housing and the base assembly between a first position in which the sleeve supports the at least three balls in the locking position, and a second position in which the sleeve allows the at least three balls to move from the locking position to the unlocking position; and a coil spring disposed between the base assembly and the housing and configured to urge the sleeve toward the first position, wherein the housing includes an aperture configured to provide access to the sleeve to allow a user to move the sleeve between the first and second positions from external the housing, wherein the holder is free from structure that is movably attached to at least one of the housing and the base assembly, and that allows the user to move the sleeve from the first position toward the second position by moving the structure relative to the at least one of the housing and the base assembly, wherein the holder is free from structure that is movably attached to the housing and that allows the user to move the follower assembly from the first position toward the second position by moving the structure relative to the housing, and wherein the sleeve includes first and second opposed openings that overlap with the first and second apertures when the apertures are viewed perpendicular to the longitudinal axis such that a passage is formed through the first and second apertures and the first and second openings, the first and second openings extending perpendicular of the longitudinal axis through the sleeve, and wherein the formed passage is configured to receive an external key, the external key allowing a user to move the sleeve from the first position toward the second position from external the housing by moving the key relative to the housing when the key is received in the formed passage.

14. The holder of claim 13, wherein the sleeve includes an internal wall, the internal wall including a first portion having a first diameter, a second portion spaced from the first portion and having a second diameter that is smaller than the first diameter, and a sloped transition portion disposed between the first and second portions, and wherein the sloped transition portion contacts the at least three balls and moves the at least three balls from the unlocking position to the locking position when the sleeve is moved from the second position to the first position.

15. The holder of claim 14, wherein the sloped transition portion is spaced from the at least three balls when the sleeve is in the second position allowing the at least three balls to move from the locking position to the unlocking position.

* * * * *